United States Patent
Rioux et al.

(10) Patent No.: US 9,474,571 B2
(45) Date of Patent: Oct. 25, 2016

(54) PERCUTANEOUS TISSUE ABLATION PROBE WITH OCCLUSIVE BODIES

(75) Inventors: Robert F. Rioux, Ashland, MA (US); Paul DiCarlo, Middleboro, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1109 days.

(21) Appl. No.: 12/251,330

(22) Filed: Oct. 14, 2008

(65) Prior Publication Data

US 2009/0099560 A1 Apr. 16, 2009

Related U.S. Application Data

(60) Provisional application No. 60/980,164, filed on Oct. 15, 2007.

(51) Int. Cl.
- *A61B 18/18* (2006.01)
- *A61B 18/14* (2006.01)
- *A61M 25/10* (2013.01)
- *A61B 17/22* (2006.01)
- *A61B 18/00* (2006.01)

(52) U.S. Cl.
CPC ....... *A61B 18/1477* (2013.01); *A61M 25/1011* (2013.01); *A61B 2017/22067* (2013.01); *A61B 2018/00589* (2013.01); *A61B 2018/1472* (2013.01); *A61B 2218/002* (2013.01); *A61M 2025/1052* (2013.01)

(58) Field of Classification Search
CPC ............ A61B 2018/00285; A61B 2018/1472; A61M 25/1011; A61M 2025/1052
See application file for complete search history.

(56) References Cited

U.S. PATENT DOCUMENTS

| | | | |
|---|---|---|---|
| 5,125,928 A | 6/1992 | Parins et al. | |
| 5,403,311 A | 4/1995 | Abele et al. | |
| 5,437,662 A | 8/1995 | Nardella | |
| 5,458,597 A | 10/1995 | Edwards et al. | |
| 5,571,088 A | 11/1996 | Lennox et al. | |
| 5,588,961 A * | 12/1996 | Leone ..................... | A61F 2/958 604/101.03 |
| 6,503,247 B2 * | 1/2003 | Swartz ............... | A61B 18/1492 606/41 |
| 6,652,515 B1 * | 11/2003 | Maguire et al. ................ | 606/41 |
| 6,773,433 B2 * | 8/2004 | Stewart et al. ................. | 606/41 |
| 6,962,588 B2 | 11/2005 | Sauvageau et al. | |
| 7,247,269 B2 * | 7/2007 | Keidar ......................... | 264/678 |
| 2003/0069570 A1 * | 4/2003 | Witzel et al. .................. | 606/28 |
| 2004/0143251 A1 * | 7/2004 | Sampson et al. .............. | 606/40 |
| 2005/0021015 A1 * | 1/2005 | Keidar ........................... | 606/27 |
| 2005/0165391 A1 * | 7/2005 | Maguire et al. ................ | 606/41 |
| 2005/0240249 A1 * | 10/2005 | Tu et al. ......................... | 607/96 |
| 2005/0245926 A1 * | 11/2005 | Edwards et al. ............... | 606/41 |
| 2007/0083194 A1 * | 4/2007 | Kunis et al. .................... | 606/41 |

(Continued)

OTHER PUBLICATIONS

Injection Gold Probe and Gold Probe, Bipolar Hemostasis Catheters, Boston Scientific Corporation (2003) (2 pages).

*Primary Examiner* — Laura Bouchelle
*Assistant Examiner* — Anh Bui (57) ABSTRACT

A tissue treatment system comprising a tissue treatment probe to be introduced in a target tissue region, wherein the probe comprises one or more perfusion ports that perfuse electrically conductive fluid to the target tissue region, one or more electrodes that deliver RF energy to the target tissue region to therapeutically treat the tissue, and at least one occlusive body that expands to occlude an anatomical vessel in or near where the probe is located in order to prevent heat generated by the delivery of the RF energy from being lost to mobile bodily fluids.

9 Claims, 10 Drawing Sheets

(56) References Cited

U.S. PATENT DOCUMENTS

| | | | |
|---|---|---|---|
| 2007/0112341 A1* | 5/2007 | Edwards et al. | 606/32 |
| 2007/0276362 A1* | 11/2007 | Rioux et al. | 606/41 |
| 2008/0091191 A1* | 4/2008 | Witzel et al. | 606/41 |
| 2009/0012518 A1* | 1/2009 | Utley | A61B 18/1492 606/41 |
| 2009/0093802 A1* | 4/2009 | Kulesa et al. | 606/33 |
| 2010/0087809 A1* | 4/2010 | Edwards et al. | 606/33 |
| 2011/0106074 A1* | 5/2011 | Kunis et al. | 606/41 |

* cited by examiner

PERCUTANEOUS TISSUE ABLATION PROBE WITH OCCLUSIVE BODIES

RELATED APPLICATION

This application claims priority to U.S. Provisional Patent Application No. 60/980,164 filed on Oct. 15, 2007. The above-noted Patent Application is incorporated by reference as if set forth fully herein.

FIELD OF THE INVENTION

The field of the invention relates generally to the structure and use of radio frequency (RF) probes for the treatment of tissue.

BACKGROUND

The delivery of radio frequency (RF) energy to target regions within solid tissue is known for a variety of purposes of particular interest to the present invention. In one particular application, RF energy may be delivered to diseased tissue regions (e.g., tumors) for the purpose of ablating predictable volumes of tissue with minimal patient trauma. Of particular relevance to the invention, it may be necessary to treat, especially ablate, target tissue with RF energy in a particular region near or adjacent to an anatomical vessel, such as a blood vessel or bronchial tube.

As an example of a treatment process, RF energy may be delivered to a target tissue region via one or more electrodes coupled to an RF generator. The transmission of the RF energy results in ion agitation of the cells in the surrounding tissue, leading to the generation of frictional heat. This causes the temperature of the cells to increase, resulting in irreversible cell damage, referred to as coagulation necrosis. A lesion is then created in the target tissue region undergoing the ablation. This technique of applying RF energy to treat diseased tissue is most often performed percutaneously, although it may also be performed during open surgery.

To more effectively treat diseased tissue with RF energy, an electrically conductive fluid, such as a saline solution, may be delivered to the target tissue receiving the RF energy. Typically, the electrically conductive fluid is delivered to the diseased target tissue percutaneously via a syringe or other similar delivery device. The introduction of electrically conductive fluid to the target tissue has been shown to increase the tissue's conductivity, thereby creating a larger legion size when RF energy induces cell necrosis. In addition, the presence of electrically conductive fluid has also been shown to reduce the local temperature of the tissue region, thereby minimizing tissue vaporization and charring during the treatment procedure.

One issue that arises when RF energy is used to treat tissue in the region of or adjacent to a vessel is that heat generated by the RF energy may be conducted away from the target vessel region by mobile fluids in the vessel itself or in surrounding vessels, creating a heat-sink effect. Because of this heat loss, the tissue targeted for treatment in the vessel region may not reach the desired temperature for effective necrosis.

The heat-sink effect may be offset during an open surgical procedure by a clamping the respective vessel, for example, with fingers or forceps, to reduce or eliminate fluid flow, such as blood flow, adjacent to or through the treatment site. This technique is called a "Pringle maneuver." However, a Pringle maneuver may not be possible during a percutaneous ablation procedure due to the difficulties of accessing the vessel.

Therefore, there is a need in the art for a treatment system that delivers electrically conductive fluid to a target vessel region while counteracting the heat sink effect by preventing, or at least minimizing, heat loss due to surrounding fluid movement when RF energy is delivered to the target vessel region.

SUMMARY OF THE INVENTION

In accordance with the present inventions, a tissue treatment probe is provided. The probe comprises one or more therapeutic electrodes carried on a distal end of the probe, one or more fluid delivery lumens, and one or more perfusion ports on the distal end of the probe in fluid communication with the fluid delivery lumen(s). The perfusion port(s) may be located proximate to the electrode(s), such that an electrically conductive fluid may be conveyed through the perfusion port(s) in close proximity to the electrode(s) to facilitate the conduction of electrical energy to, from, or between the electrode(s).

By way of non-limiting example, the therapeutic electrode(s) may be arranged as a plurality of electrodes, wherein the perfusion port(s) is axially located between the electrodes. In another embodiment, the electrode(s) comprises a plurality of interleaved spiral electrodes, wherein the perfusion port(s) comprises a plurality of perfusion ports axially located between the adjacent windings of the electrodes.

The probe further comprises one or more radially expandable occlusive bodies carried on the distal end of the probe shaft, which are capable of being used to at least partially occlude the flow of fluid through an anatomical vessel. The perfusion port(s) and the electrode(s) are axially located on one side of the occlusive body(ies). Thus, although the present inventions should not be so limited in their broadest aspects, the expansion of the occlusive body(ies) in an anatomical vessel reduces the amount of mobile bodily fluids contacting the distal end of the probe, thus reducing the heat-sink effect that would otherwise result from the mobile fluids carrying away heat generated by electrical energy conveyed to, from or between the electrode(s)

As a non-limiting example, each of the occlusive body(ies) may comprise a balloon having an interior region in fluid communication with the fluid delivery lumen(s). Thus, in one embodiment, fluid conveyed through the fluid delivery lumen(s) fills the interior region of the balloon and causes the balloon to expand. In this case, the fluid perfusion and occlusion functions may be performed simultaneously. In an alternative embodiment, each of the occlusive body(ies) comprises a balloon having an interior region in fluid communication with a separate fluid delivery lumen, for example, an inflation lumen. In this case, the fluid perfusion and occlusion functions may be performed independently.

In accordance with a first aspect of the present inventions, the electrode(s) comprises a plurality of electrodes carried on the distal end in a multi-polar arrangement for conducting electrical energy, such that energy is conducted between the electrodes on the distal end. In one embodiment, the plurality of electrodes is in a bipolar arrangement. Although the present inventions should not be so limited in their broadest aspects, the location of perfusion port(s) between multipolar electrode(s) allows electrically conductive fluid to be precisely located between the electrodes where it is most needed.

In accordance with a second aspect of the present inventions, the occlusive body(ies) comprises two occlusive bodies carried on the distal end of the probe, such that the electrode(s) and the perfusion port(s) are axially located between the two occlusive bodies. While the present inventions should not be so limited in their broadest aspects, the use of two occlusive bodies further minimizes the heat-sink effect, as expansion of the two occlusive bodies occludes the vessel both distally and proximally to the electrode(s). Additionally, more of the fluid conveyed through the perfusion port(s) may remain between the two occlusive bodies.

In accordance with a third aspect of the present inventions, a method of treating tissue comprises introducing the treatment probe into an anatomical vessel (e.g., a blood vessel), radially expanding the occlusive body(ies) to at least partially occlude the vessel, delivering an electrically conductive fluid through the perfusion port(s) into the vessel, and therapeutically conveying electrical energy to, from, or between the electrode(s) via the electrically conductive fluid to treat the tissue. In one method, the treatment probe is inserted into the anatomical vessel to treat tissue (e.g., tumorous tissue) external to the vessel. In another method, the probe is introduced percutaneously into the anatomical vessel using a guiding member inserted in a central lumen of the probe. Although the present inventions should not be so limited in their broadest aspects, the occlusion of the vessel by the occlusive body(ies) and resulting reduction of the heat-sink effect promotes more effective treatment of the tissue.

In accordance with a fourth aspect of the present inventions, a tissue treatment system comprises the treatment probe, a source of electrical energy coupled to the electrode(s), and a source of electrically conductive fluid coupled to the fluid delivery lumen(s). As a non-limiting example, the tissue treatment system may be used to treat tissue, as described above, by conveying electrical energy between the source of electrical energy and electrode(s) and conveying fluid from the source of electrically conductive fluid to the perfusion port(s)

Other and further aspects and features of the invention will be evident from reading the following detailed description of the preferred embodiments, which are intended to illustrate, not limit, the present inventions.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

Figure 1:
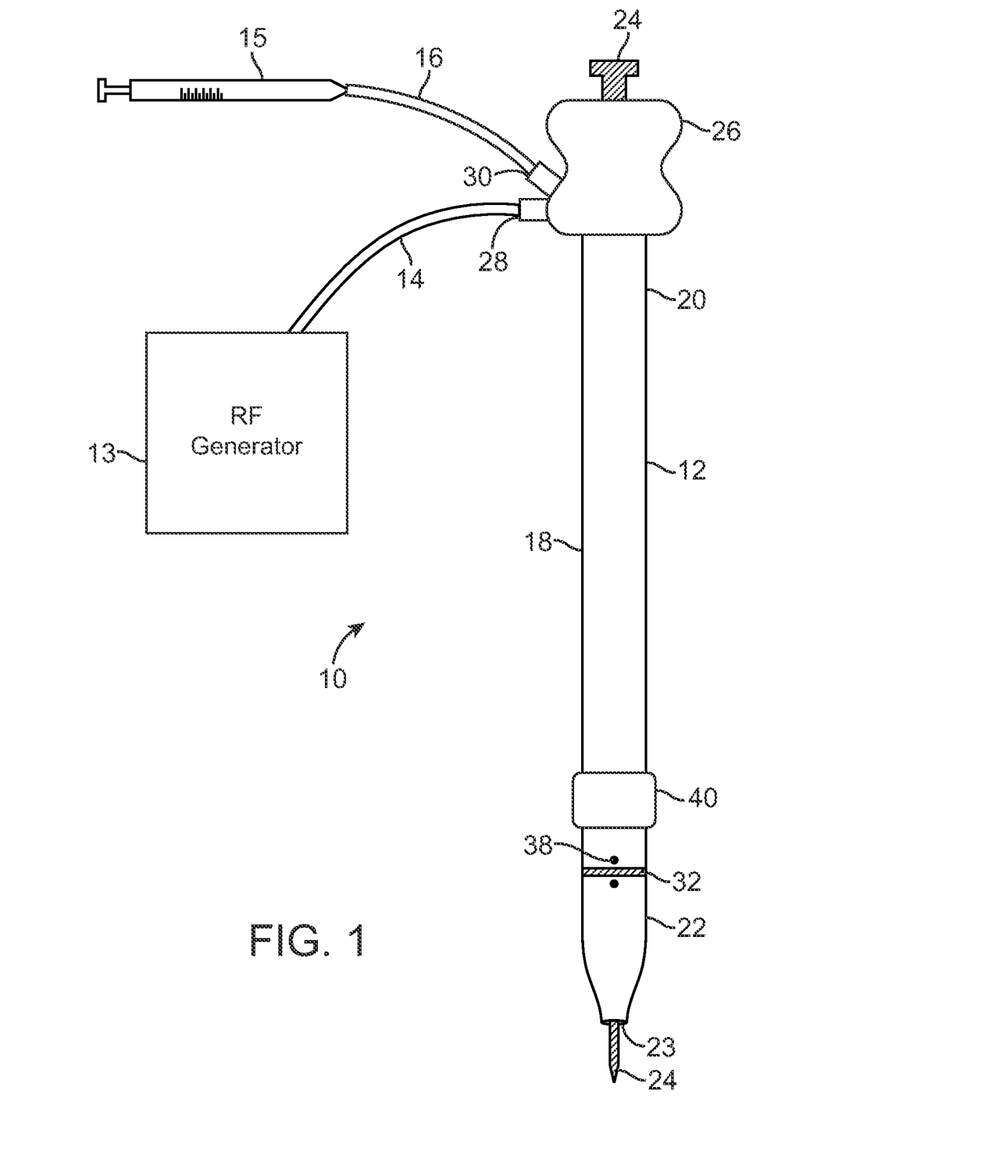
FIG. 1 illustrates a plan view of a tissue treatment system arranged in accordance with one embodiment of the present inventions.
Figure 2:
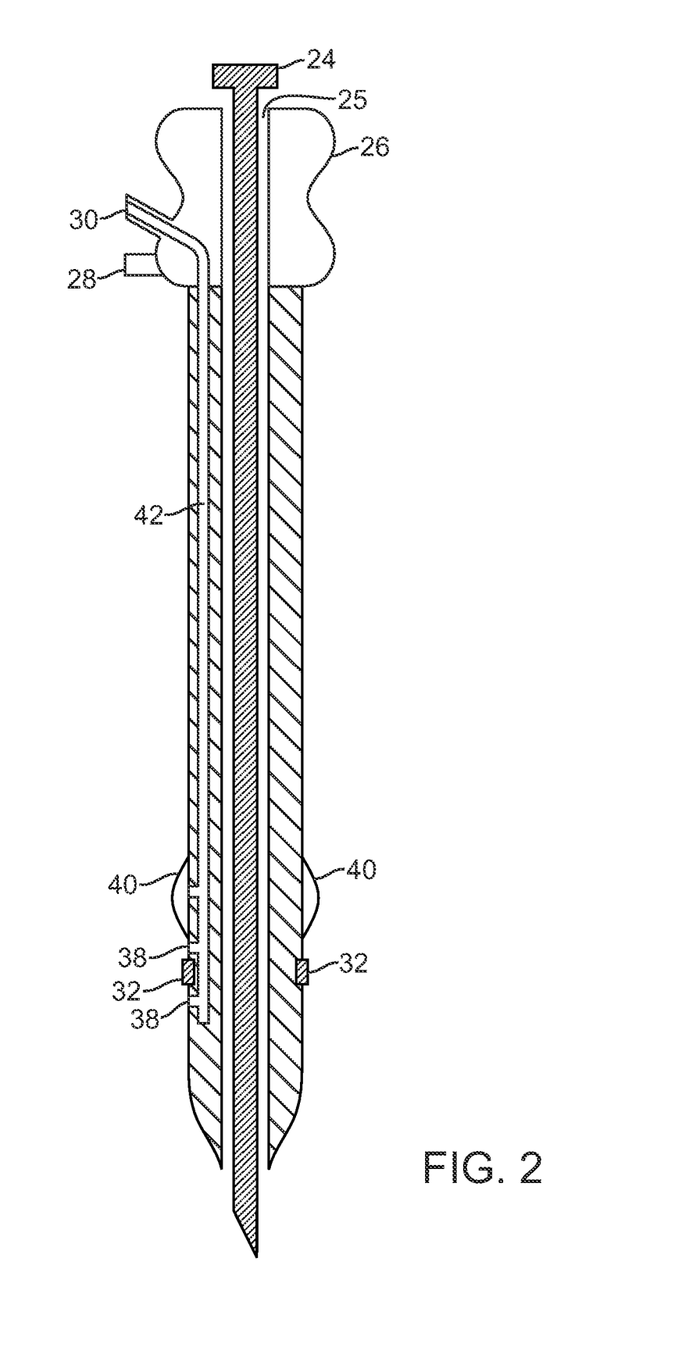
FIG. 2 illustrates a cross-sectional view of a tissue treatment probe used in the tissue treatment system of FIG. 1.

Referring to FIGS. 1 and 2, a tissue treatment system 10 constructed in accordance with one embodiment of the present inventions, will now be generally described. A particular type of treatment to which the system 10 is directed is tissue ablation. The tissue treatment system 10 generally comprises a tissue treatment probe 12, an ablation source 13 (in particular a source of radio frequency (RF) energy) electrically coupled to the probe 12 via a cable 14 for delivering ablation energy to tissue, and a source of fluid 15 fluidly coupled to the treatment probe 12 via a tube 16 for delivering an electrically conductive fluid to the tissue.

The probe 12 is configured for introduction into the body of a patient for treatment of target tissue. Preferably, the probe 12 takes the form of a flexible catheter sized for entry in an anatomical vessel. As used here, a vessel refers to any anatomical duct, canal, or other tube containing or conveying bodily fluid (liquid or air). Thus, the term vessel may refer to blood vessels, such as a portal vein, or air tubes, such as a bronchial tube. The probe 12 comprises an elongated shaft 18 having a proximal end 20 and a distal end 22. The probe 12 is configured to receive a guiding member or stylet 24. As will be described in further detail below, the stylet 24 can puncture skin, while lending rigidity to the probe 12, to guide the probe 12 to the target vessel region. In the illustrated embodiment, the distal end 22 of the probe 12 has a blunted end with a terminal orifice 23 from which the stylet 24 may extend.

The probe 12 further comprises a handle assembly 26 carried by the proximal end 20 of the shaft 18. The handle assembly 26 has an ergonomically-shaped handle component 26 for gripping and maneuvering the probe 12, an electrical connector 28 configured to mate with the cable 14 from the RF energy source 13, and a fluid inlet port 30 configured to mate with the fluid tube 16 from the fluid source 15.

The probe 12 further comprises one or more electrodes 32 carried by the distal end 22 of the shaft 18. The electrode 32 is coupled to the electrical connector 28 with one or more RF wires, so that RF energy can be conveyed from the RF energy source 13 to the therapeutic electrode 32, causing tissue in contact with or proximate to the electrode 32 to be treated by the RF energy.

The probe 12 further comprises a plurality of perfusion ports 38 carried by the distal end 22 of the shaft 18. The perfusion ports 38 are coupled to the fluid inlet port 30 via a fluid lumen 42 (shown in FIG. 2) extending through the probe shaft 18, so that fluid can be conveyed from the fluid source 15, allowing fluid to perfuse through the perfusion ports 38 to the surrounding region. The perfusion ports 38 are axially located near or approximately adjacent to the electrode 32. In this manner, fluid can perfuse through the perfusion ports 38 in close proximity to or in contact with the electrode 32. This is especially significant when the fluid is an electrically conductive fluid, so that the conductivity of the surrounding tissue region is increased for more effective treatment of the target tissue.

The probe 12 further comprises one or more expandable occlusive bodies 40 carried by the distal end 22 of the shaft 18. In the illustrated embodiment, the expandable occlusive body 40 takes the form of a balloon. The balloon 40 is fluidly coupled to the fluid inlet port 30 with the fluid lumen 42, so that fluid can be conveyed from the fluid source 15 to the interior of the balloon 40, thereby causing the balloon 40 to radially expand and occlude a vessel. As will be described in further detail below, more than one balloon 40 may be carried by the distal end 22 to occlude the vessel. Significantly, occlusion of the vessel allows the fluid conveyed by the perfusion ports 38 to be at least partially contained within the vessel to maximize the efficiency of the tissue ablation procedure.

Further details of the treatment probe 12 features will now be described. Referring still to FIG. 1, the probe shaft 18 has a suitable length, typically in the range from 5 cm to 30 cm, preferably from 10 cm to 25 cm, and an outer diameter consistent with its intended use, typically being from 0.7 mm to 5 mm, usually from 1 mm to 4 mm. The shaft 18 can be composed of a rigid material, but is preferably composed of a flexible material such that it has adequate maneuverability for introduction into a vessel. Additionally, the blunted distal end 22 of the shaft 18 minimizes any damage that the probe 12 may otherwise cause to the vessel wall.

Although the shaft may be composed of a flexible material, it is desirable for the probe 12 to be rigid when it is inserted through skin and into the target vessel. As briefly discussed above, the stylet 24 may be used to impart rigidity to the probe 12 for insertion into a patient by inserting the stylet 24 through a central lumen 25 which extends longitudinally through the approximate center of the probe shaft 18, as shown in FIG. 2. The stylet 24 is insertable into the central lumen 25 through an opening of the central lumen 25 at the proximal end 20. The stylet 24 has a sharpened end for puncturing skin or other tissue. When the stylet 24 is inserted in the central lumen 25, it may protrude from both the proximal end 20 and the distal end 22 at the same time. In this manner, the stylet 24 can puncture a patient's skin and carry the probe 12 to the target vessel while being controlled at the proximal end 20. Furthermore, the stylet 24 can be retracted through the central lumen 25 toward the proximal end 20 once the distal end 22 is located in the target vessel, so that the portion of the probe 12 within the vessel is more flexible and the distal end 22 can be advanced toward the target tissue site without damaging the vessel.

As an alternative to using the stylet 24 to advance the probe, the probe 12 may be inserted through a rigid introducer sheath (not shown) inserted through a puncture in a patient's skin and extending toward the target vessel. In this manner, the probe 12 is advanced through the sheath to the target vessel region, after which the sheath is retracted or removed and the distal end 22 can be advanced toward the target tissue site.

Figure 3:
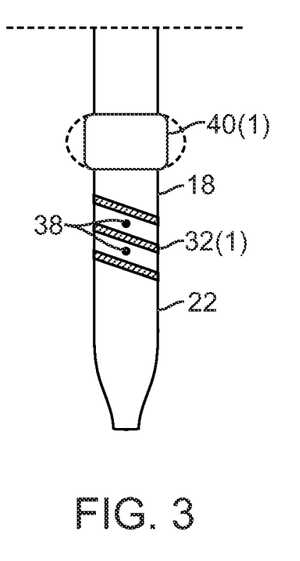
FIG. 3 illustrates a partially cutaway, side view of a distal portion of one embodiment of the tissue treatment probe of FIG. 2.

Referring to FIG. 3, the one or more electrodes 32 may take the form of a single electrode 32(1) that is spirally wrapped around the circumference of the probe shaft 18. The spaces between the electrode 32(1) windings provide a desirable location for the perfusion ports 38, which will be discussed later in further detail. The electrode 32(1) may be arranged in a monopolar fashion, such that the current will pass from the electrode 32(1), which is configured to concentrate the energy flux in order to have an injurious effect on the surrounding tissue, to a dispersive electrode (not shown), which is located remotely from the electrode and has a sufficiently large area (typically 130 $cm^2$ for an adult), so that the current density is low and non-injurious to surrounding tissue. The dispersive electrode may be attached externally to the patient, e.g., using a contact pad placed on the patient's flank.

Figure 4:
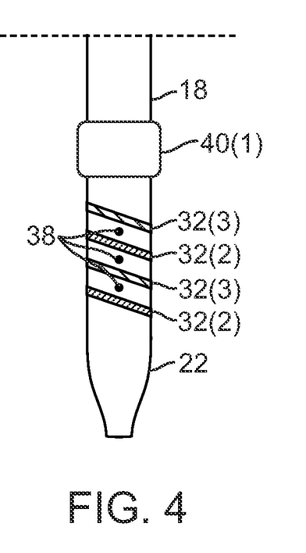
FIG. 4 illustrates a partially cutaway, side view of a distal portion of an alternative embodiment of the tissue treatment probe of FIG. 2.

As shown in FIG. 4, the one or more electrodes 32 may take the form of two electrodes 32(2), 32(3) that are spirally wrapped in parallel around the circumference of the probe shaft 18, providing spaces between the windings where the perfusion ports 38 may be located. The electrodes 32(2), 32(3) may be arranged in a bipolar fashion such that when the RF energy is conveyed to the electrodes 32(2), 32(3), the RF current passes between the electrodes 32(2), 32(3); i.e., between a positive one of the electrodes 32(2) and 32(3) and a negative one of the electrodes 32(2) and 32(3), thereby concentrating the energy flux in order to have an injurious effect on the tissue between the electrodes 32(2) and 32(3). In a bipolar arrangement, the positive and negative electrodes 32(2) and 32(3) will be insulated from each other in any regions where they would or could be in contact with each other during the power delivery phase.

Referring still to FIGS. 3 and 4, the perfusion ports 38 are axially located on the distal end 22 of the shaft 18, so that fluid, particularly electrically conductive fluid, may be conveyed through the perfusion ports 38 to contact the surrounding target vessel region. The perfusion ports 38 are preferably a circular or oval shape, having a width of about 0.5-2.0 mm. While an embodiment of the invention may have only one perfusion port 38 on the distal end 22, it is desirable to have a plurality of perfusion ports 38 in order to maximize the perfusion of liquid in the target vessel region. The perfusion ports 38 are located near the electrode(s) 32, and in particular, at least one port 38 is located between the windings of the electrode 32(1) or electrodes 32(2), 32(3), as shown in FIGS. 3 and 4. In this manner, electrically conductive fluid is discharged through the perfusion ports 38 between the windings, so that the conductivity of the surrounding tissue region is increased when the RF energy is delivered to the electrodes 32. This increased conductivity of the surrounding tissue results in more effective tissue treatment.

FIGS. 3 and 4 illustrate the perfusion ports 38 as being circumferentially aligned on the probe 12. This embodiment is advantageous, for example, when the target tissue to be treated is only at one side portion of a vessel wall. Then, the perfusion ports 38 may be aligned toward the target tissue to maximize the amount of fluid conveyed directly toward the target tissue. This embodiment may also include a marker (not shown) on the handle 26 aligned with the perfusion ports 38 so that a user may refer to the marker, in cooperation with viewing technology, to align the perfusion ports 38.

Figure 5:
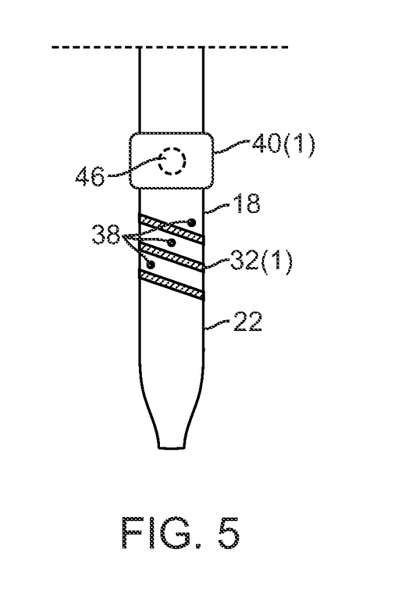
FIG. 5 illustrates a partially cutaway, side view of a distal portion of another alternative embodiment of the tissue treatment probe of FIG. 2.

While FIGS. 3 and 4 illustrate a single set of aligned perfusion ports 38, additional sets of aligned ports 38 may be provided. For example, another set of aligned perfusion ports 38 may be provided on the probe 12 opposite the first set of aligned perfusion ports 38; i.e., 180 degrees circumferentially offset from each other. In an alternative arrangement, the perfusion ports 38 may be circumferentially staggered, as shown in FIG. 5. This embodiment is advantageous when the target tissue surrounds the target vessel or is otherwise circumferentially located at various points about the target vessel. In this manner, the fluid may be conveyed around the circumference of the probe 12 so that it is directed toward more of the target tissue.

Figure 7:
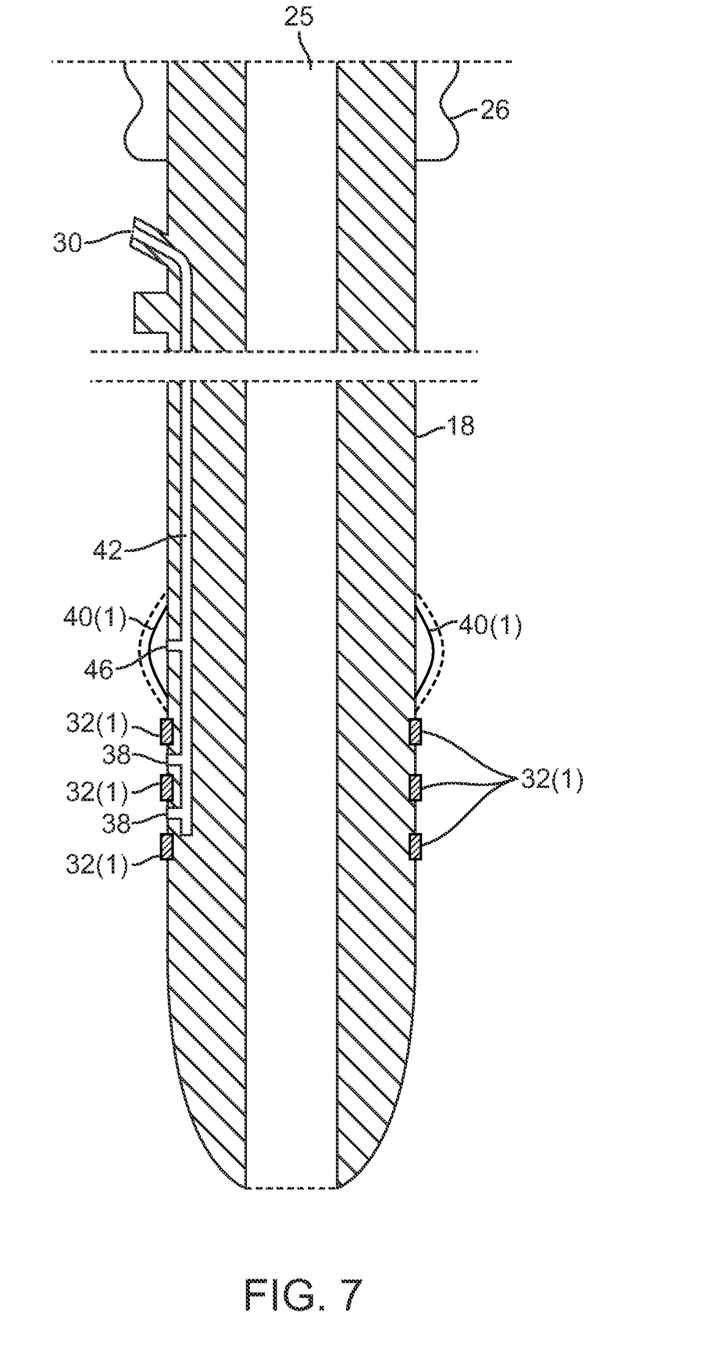
FIG. 7 illustrates a partially cutaway, cross-sectional view of an alternative embodiment of the tissue treatment probe of FIG. 2.

Now referring to FIG. 7, the perfusion lumen 42 that fluidly couples the fluid inlet port 30 and the perfusion ports 38 is located adjacent or nearly adjacent to an interior surface of the probe shaft 18 and extends through the interior of the probe shaft 18 from the fluid inlet port 30 to the perfusion ports 38. In another embodiment of the invention, the perfusion lumen 42 may be located external to the probe shaft 18. However, this may increase the diameter of the probe 12, making percutaneous insertion of the probe less suitable. While the probe 12 may only have one perfusion lumen 42, as illustrated in FIG. 2, it may be desirable to have a plurality of perfusion lumens 42. For example, if more than one set of aligned perfusion ports 38 are provided, or if the perfusion ports 38 are staggered as shown in FIG. 5, the probe 12 may employ a plurality of perfusion lumens 42 such that each perfusion port 38 or set of perfusion ports 38 has a perfusion lumen 42 leading directly to it. Alternatively, a single perfusion lumen 42 may lead to the circumferentially staggered perfusion ports 38 by meandering or diagonally aligning the lumen 42 between the ports 38. Another embodiment may have perfusion ports 38 on opposing sides of the shaft 18 and in fluid communication with two or more perfusion lumens 42 also on opposing sides of the shaft 18.

Again referring to FIG. 3, the one or more balloons 40 may take the form of a single balloon 40(1) carried on the distal end 22 of the probe 12 near the electrode 32(1) and the perfusion ports 38. The balloon 40(1) may be mounted circumferentially around an outer surface of the probe shaft 18 using suitable means, such as bonding with a medical-grade adhesive or other suitable adhesive. The balloon 40(1) is radially expandable about the distal end 22 of the probe shaft 18, having a diameter when fully expanded that is consistent with or slightly greater than the inner diameter of the vessel in which the balloon 40(1) is introduced, e.g., about one to three centimeters.

Still referring to FIG. 3, the electrode 32(1) and the perfusion ports 38 are located on one side of the balloon 40(1), preferably a distal side of the balloon 40(1), so that the expanded balloon 40(1) occludes the target vessel on the proximal side of the electrode 32(1) and the perfusion ports 38. Thus, mobile bodily fluids approaching the target vessel region from the proximal side of the balloon 40(1) are prevented from entering the target vessel region. It can therefore be appreciated that whenever the balloon 40(1) is expanded to occlude a vessel, the heat is prevented from being drawn away from the target vessel region distal to the balloon 40(1), and thus, the adjacent target tissue outside of the vessel, because bodily fluids are partly or completely blocked from transporting heat away from the RF energy delivery site. This promotes more efficient and complete treatment of the target tissue.

Figure 6:
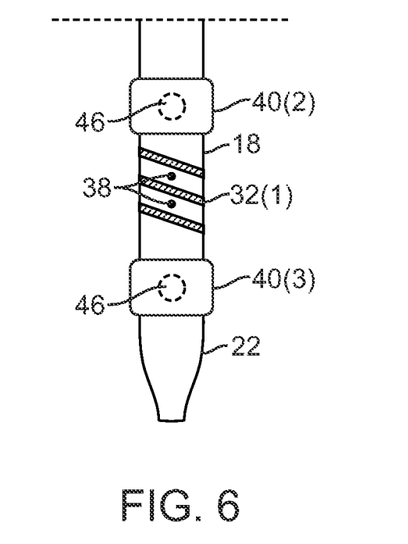
FIG. 6 illustrates a partially cutaway, side view of a distal portion of still another alternative embodiment of the tissue treatment probe of FIG. 2.

Alternatively, as illustrated in FIG. 6, the one or more balloons 40 may take the form of a pair of proximal and distal balloons 40(2) and 40(3). The proximal balloon 40(2) is preferably located proximal to the electrode 32(1), and the distal balloon 40(3) is preferably located distal to the electrode 32(1) and the perfusion ports 38, such that the electrode 32(1) and the perfusion ports 38 are between the balloons 40(2), 40(3). In this embodiment, when both balloons 40(2), 40(3) are expanded, the target vessel is occluded both proximally and distally to the electrode 32(1) and the perfusion ports 38. The two balloons 40(2), 40(3) may also be used on the embodiment having two electrodes 32(2), 32(3), wherein the second balloon 32(3) is located distally to both electrodes 32(2), 32(3). The advantage to having two balloons 40(2), 40(3) expanded is that mobile bodily fluids are prevented from entering the target vessel region from either a proximal or distal side of the electrode 32(1) and transporting heat away from the target vessel region. Additionally, more of the electrically conductive fluid is contained between the balloons 40(2), 40(3) in the target vessel region to promote conductivity of the RF energy.

To cause the balloon 40(1), or balloons 40(2), 40(3) depending on the embodiment used, to expand and occlude the target vessel, the balloon 40(1) is filled with a fluid medium, such as a liquid. As shown in FIG. 7, this is achieved by conveying fluid to an interior region of the balloon 40(1) through an inflation port 46 axially located on the shaft 18. To this end, the inflation port 46 is fluidly coupled with the fluid inlet port 30 by the perfusion lumen 42. In this manner, as fluid is delivered to the perfusion ports 38, fluid is also delivered to the inflation port 46 to expand the balloon 40(1).

Figure 8:
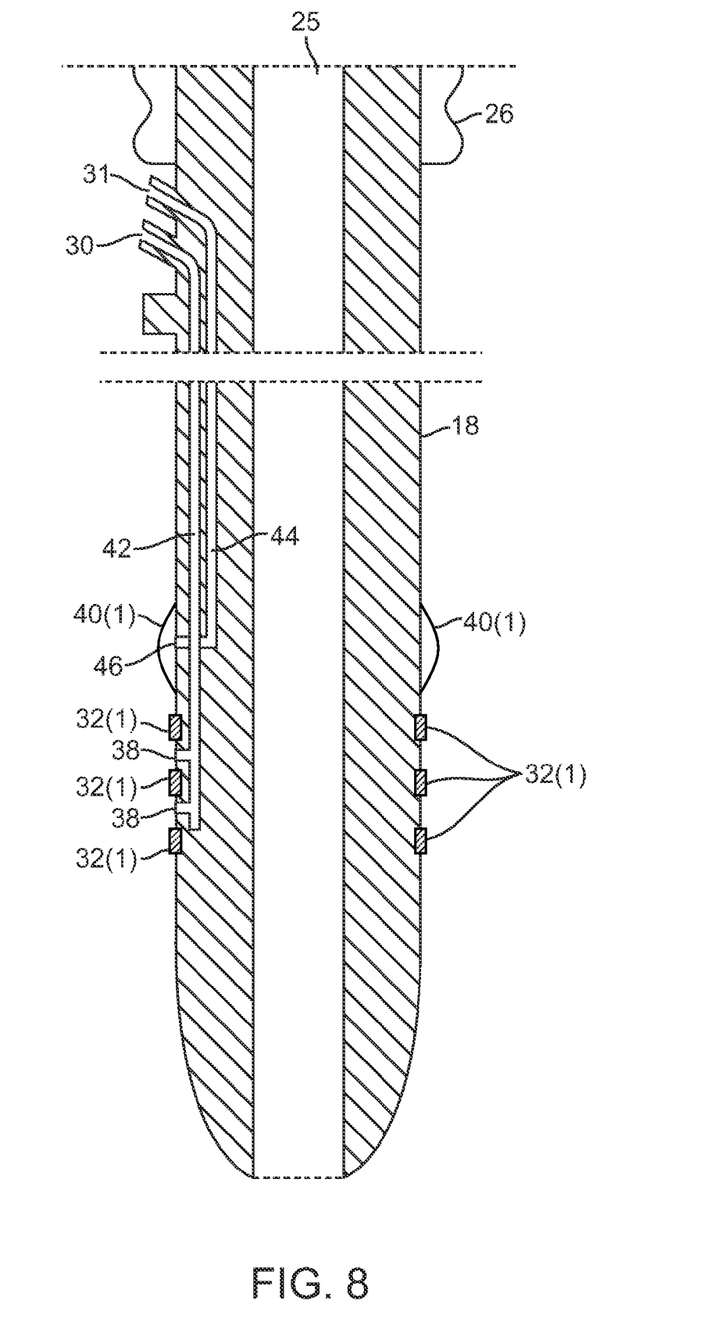
FIG. 8 illustrates a partially cutaway, cross-sectional view of another alternative embodiment of the tissue treatment probe of FIG. 2.

Alternatively, as shown in FIG. 8, an inflation lumen 44, separate from the perfusion lumen 42, fluidly couples the inflation port 46 to an additional fluid inlet port 31 located on the handle assembly 26. For the embodiment having two balloons 40(2), 40(3), the inflation lumen 44 may extend to the inflation port 46 associated with both balloons 40(2), 40(3). Alternatively, each balloon 40(2) or 40(3) may have a dedicated inflation lumen 44 such that only one inflation lumen 44 extends to each balloon 40(2), 40(3). Having an inflation lumen 44 separate from the perfusion lumen 42 may be advantageous if the user desires to make the occlusion and fluid perfusion functions independent from each other, for example, if the user desires to perform one of these functions before the other.

To deliver fluid to the additional fluid inlet port 30(2), the same fluid source 15 used with the fluid inlet port 30 dedicated to the perfusion lumen 42 may be used. In this embodiment, the fluid source 15 has two tubes (not shown), each extending to one of the fluid inlet ports 30, 31 and having valves (not shown) on the respective tubes 16(1), 16(2) (not shown) for independently controlling fluid delivery to the inlet ports 30, 31. Alternatively, a separate fluid source (not shown) in fluid communication with the additional fluid inlet port 31 may be used, so that each fluid inlet port 30, 31 has a dedicated tube and valve assembly (not shown) for controlling fluid delivery.

The fluid source 15 can be a standard syringe that is insertable through the fluid inlet port 30, and also the additional fluid port 31, if included. Alternatively, a pump with tubing or other suitable fluid delivery mechanism may be used. The RF generator 13 used in the tissue treatment system 10 may be a conventional general purpose electrosurgical power supply operating at a frequency in the range from 300 kHz to 9.5 MHz, with a conventional sinusoidal or non-sinusoidal wave form. Power supplies for the RF energy are available from many commercial suppliers, such as Valleylab, Aspen, Bovie, and Ellman. Most general purpose electrosurgical power supplies, however, are constant current, variable voltage devices and operate at higher voltages and powers than would normally be necessary or suitable. Thus, such power supplies will usually be operated initially at the lower ends of their voltage and power capabilities, with voltage then being increased as necessary to maintain current flow. More suitable power supplies will be capable of supplying a current, such as an ablation current, at a relatively low fixed voltage, typically below 200 V (peak-to-peak). Such low voltage operation permits use of a power supply that will significantly and passively reduce output in response to impedance changes in the target tissue. The output will usually be from 5 W to 300 W, usually having a sinusoidal wave form, but other wave forms would also be acceptable. Power supplies capable of operating within these ranges are available from commercial vendors, such as Boston Scientific Therapeutics Corporation. Preferred power supplies are models RF-2000 and RF-3000, available from Boston Scientific Corporation.

Having described the structure of the tissue treatment system 10, its operation in treating, and in particular ablating, target tissue T adjacent a target vessel region TVR of a vessel V, will now be described. The target tissue T may be located anywhere in the body where hyperthermic exposure may be beneficial and may be comprised of a vessel or a network of vessels. In the illustrated embodiment shown in FIG. 9, the target tissue T comprises a tumor adjacently located to a wall W of vessel V.

The volume to be treated will depend on the size of the tumor T or other lesion, typically having a total volume from 1 $cm^3$ to 150 $cm^3$, and often from 2 $cm^3$ to 35 $cm^3$. The peripheral dimensions of the treatment region may be regular, e.g., spherical or ellipsoidal, but will more usually be irregular. The target tissue, or tumor, T may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor T or other lesion being treated, either intraoperatively or externally.

Figure 9:
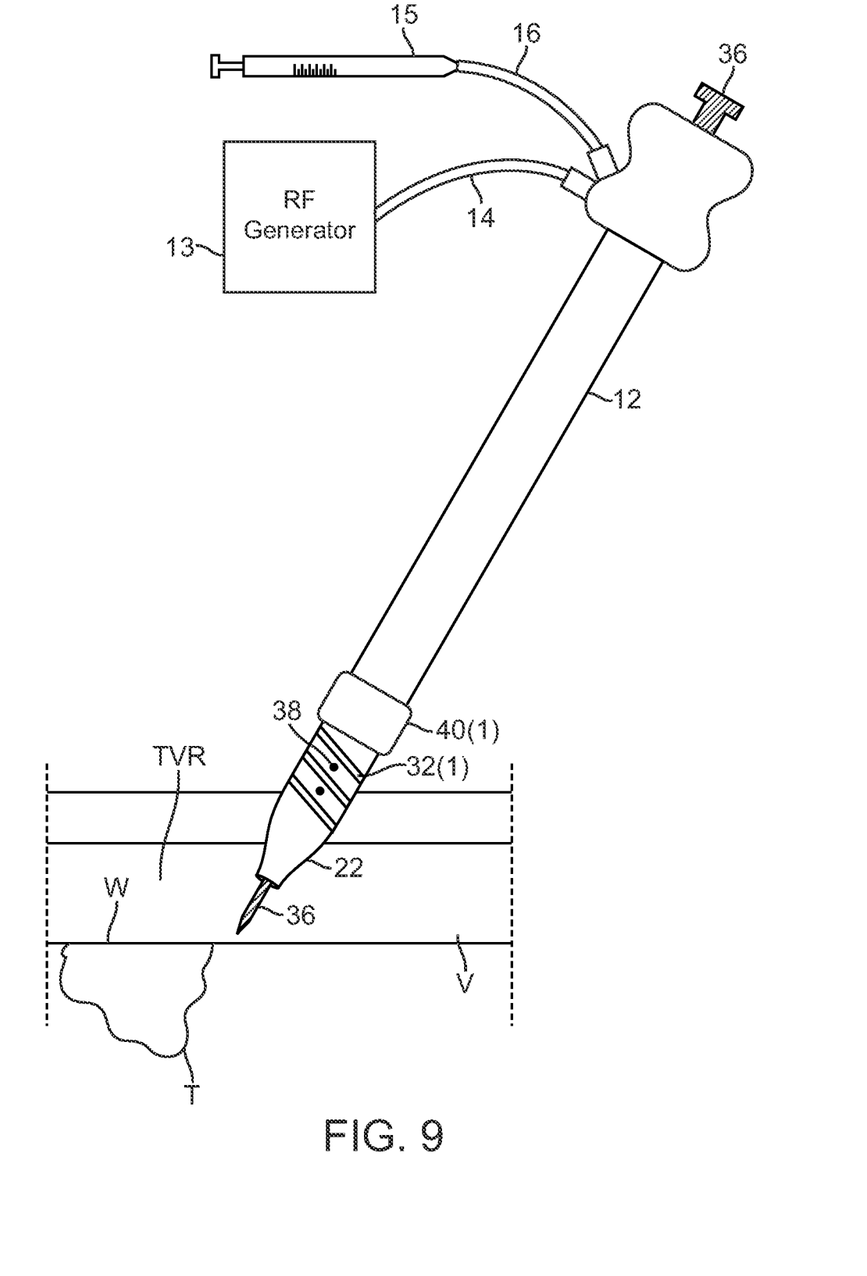
FIGS. 9-13 illustrate a method for using the tissue treatment system of FIG. 1.

Continuing with the description of a method for using the tissue treatment system 10, the probe 12 is first introduced into the vessel V in a patient or proximate thereto. To do so, the stylet 24 is inserted in the central lumen 25 of the probe 12, such that the stylet 24 protrudes from the terminal orifice 23 of the probe 12 to puncture the patient's skin and carry the probe 12 to the target vessel region TVR where the tumor T is located. Pressure is applied to the stylet 24 from the proximal end 20 to puncture the patient's skin and then advance the stylet 24 that carries the probe 12 to the target vessel region TVR, as shown in FIG. 9. If a distal portion of the stylet 24 is echogenic, the stylet 24 may cause the probe 12 to be more accurately positioned for treatment of the tissue by using ultrasound or other similar locating technology.

Figure 10:
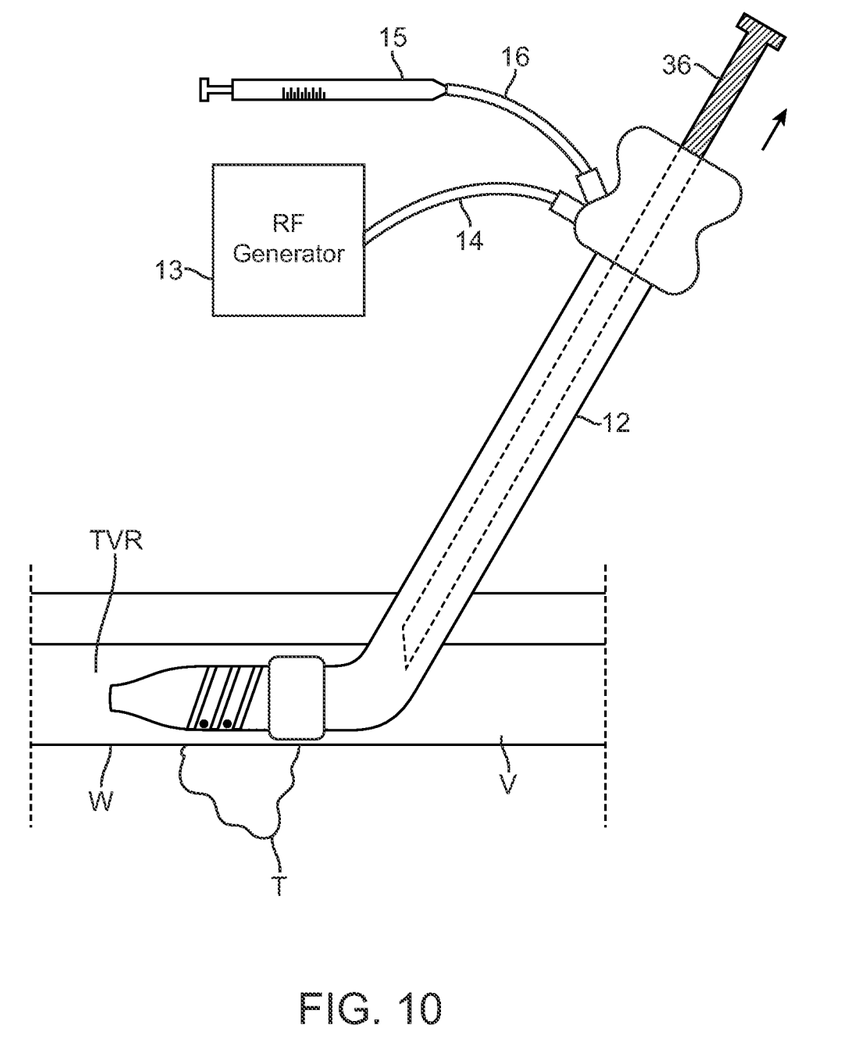

Once the distal end 22 is located in or proximate to the target vessel region TVR, the stylet 24 is retracted through the proximal end 20. The probe 12, now less rigid, can then be advanced through the target vessel region TVR, as shown in FIG. 10, to the portion of the vessel wall W adjacent to the tumor T without damaging the vessel V or any adjacent healthy bodily tissue. Alternatively, the probe 12 may be pushed through an introducer sheath (not shown) already introduced through the patient's skin, and furthermore extending to the target vessel region TVR. Once the probe 12 is positioned at or near the target vessel region TVR, the sheath may be removed and the probe 12 advanced to or through the target region TVR to the portion of the vessel wall W adjacent to the tumor T.

Figure 11:
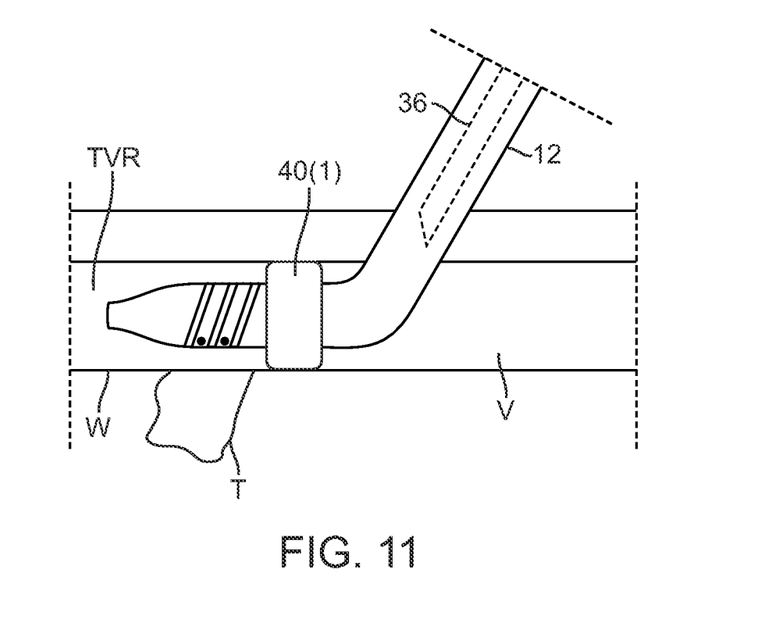
Figure 12:
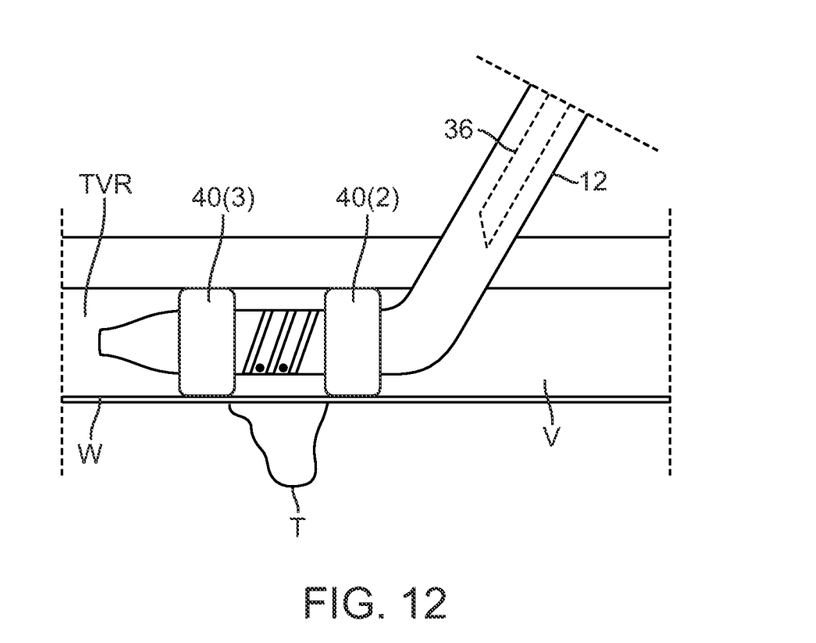

Once the distal end 22 positioned near the tumor T for treatment, the balloon 40(1) is expanded, as shown in FIG. 11. In the case where the same lumen is used for the occlusion and fluid perfusion functions, the balloon 40(1) is expanded by conveying fluid, particularly electrically conductive fluid, from the fluid source 15 through the fluid inlet port 30 to the perfusion lumen 42 and then through the inflation port 46 to the interior of the balloon 40(1). FIG. 11 illustrates the vessel being occluded by the balloon 40(1) on the proximal side of the electrode 32(1). If two balloons 40(2), 40(3) are used, as shown in FIG. 12, the same steps may be taken to expand the two balloons 40(2), 40(3), namely conveying fluid from the fluid source 15 through the fluid inlet port 30 to the perfusion lumen 42 and then through the inflation port 46 to the interior of the balloons 40(2), 40(3). As the balloon 40(1), or balloons 40(2), 40(3) depending on the embodiment used, is expanded, the electrically conductive fluid is also conveyed through the perfusion lumen 42 and out into the target vessel region TVR via the perfusion ports 38.

If separate lumens 42, 44 are used to perform the occlusion and fluid perfusion functions, the balloon 40(1) is expanded by conveying fluid from the fluid source 15, or a separate fluid source, to the additional inlet port 31. The fluid is then conveyed through the inflation lumens 44 to the inflation port 46, causing the balloon 40(1) to expand and thus occlude the vessel V. After the balloon 40(1) is expanded, electrically conductive fluid is conveyed through the fluid inlet port 30 to the perfusion lumen 42 and then through the perfusion ports 38 into the target vessel region TVR.

Then, in the case of a monopolar arrangement (i.e., the probe 12 with a single electrode 32(1)), the RF energy is conveyed from the RF generator 13 along the cable 14 to the electrical connector 28, and then along an RF wire (not shown) in the probe shaft 18 to the electrode 32(1). The RF energy is then conveyed from the electrode 32(1) via the electrically conductive fluid, through the vessel wall, and then through the adjacent tissue of the tumor T, where it is returned back to the RF generator 13 via the dispersive electrode (not shown). As a result, the tumor T is therapeutically ablated.

Figure 13:
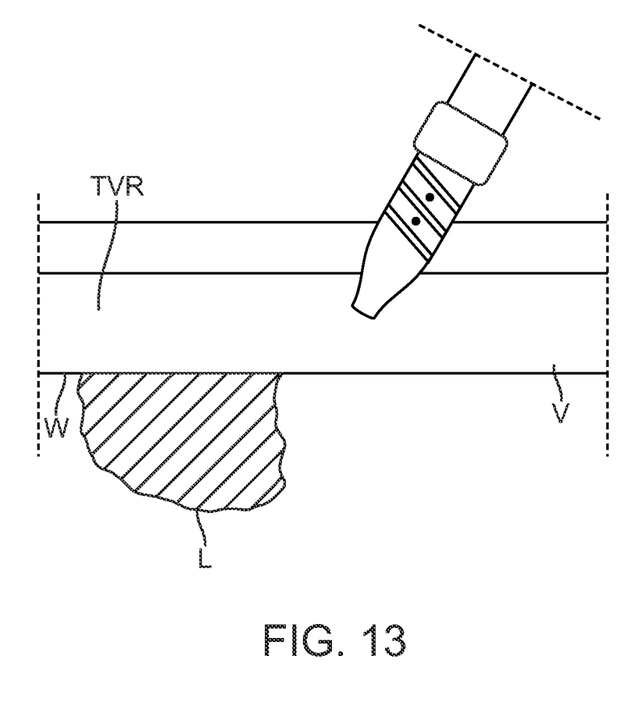

In the case of a bipolar arrangement (i.e. the probe 12 with two electrodes 32(2), 32(3)), the RF energy is conveyed from the RF generator 13 along the cable 14 to the electrical connector 28, and then along RF wire (not shown) in the probe shaft 18 to one of the electrodes 32(2), 32(3). The RF energy is then conveyed from the one electrode 32(2) or 32(3) via the electrically conductive fluid, through the vessel wall, and then through the adjacent tissue of the tumor T, where it is returned back to the other electrode 32(2) or 32(3) via the electrically conductive fluid, and back to the RF generator 13 via an RF wire (not shown) in the probe shaft 18, electrical connector 28, and cable 14. As a result, the tumor T is therapeutically ablated, thereby forming a lesion L, as shown in FIG. 13.

As the RF energy is conveyed from the electrode 32(1) or between the electrodes 32(2), 32(3), the occlusion of the vessel V by the balloon 40(1) minimizes or prevents mobile bodily fluids from entering the region where the RF energy is being conveyed. This in turn minimizes or prevents the electrically conductive fluid from being washed away, and minimizes or prevents the heat-sink effect otherwise created by the flow of the bodily fluids through the vessel V adjacent the tumor T, thereby making a more efficient ablation procedure. For the embodiment of the probe 12 having two balloons 40(2), 40(3), any electrically conductive fluid that would have been washed away or any heat-sink effect that would have occurred if only a single balloon 40(1) were used, would be further minimized, thereby providing an even more efficient ablation procedure.

Following the treatment, the balloon 40(1) is deflated by applying a vacuum to the perfusion lumen 42 or the inflation lumen 44, depending on the type of lumen used, at the fluid inlet port 30 or 31 to remove the fluid from the balloon 40(1). Vacuum may be applied with a syringe, suction pump, or other similar assembly (not shown). The same deflation method may also be used for the two balloons 40(2), 40(3).

After deflation of the balloon 40(1), or balloons 40(2), 40(3), the probe 12 may be extracted from the vessel V. This may be achieved by pulling the probe 12 at the proximal end 20 to retract the probe 12 out of the vessel V and then out of the patient.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

We claim:

1. A method for treating tissue, comprising:
   introducing a tissue treatment probe into an anatomical vessel; the tissue treatment probe comprising:
   a probe shaft having a distal end;
   a plurality of therapeutic electrodes carried on the distal end of the probe shaft;
   a fluid delivery lumen;
   at least one perfusion port on the distal end of the probe shaft in fluid communication with the fluid delivery lumen; and
   a radially expandable occlusive body carried on the distal end of the probe shaft, wherein the occlusive body is proximal to the at least one perfusion port and the plurality of therapeutic electrodes, and wherein the at least one perfusion port and the plurality of therapeutic electrodes are axially located on one side of the occlusive body;
   radially expanding the occlusive body to fully occlude the anatomical vessel;
   delivering an electrically conductive fluid through the at least one perfusion port into the anatomical vessel;
   therapeutically conveying electrical energy between the plurality of electrodes via the electrically conductive fluid to treat the tissue, wherein the tissue comprises tumorous tissue external to the anatomical vessel; and
   deflating the radially expanded occlusive body, after the tissue has been treated, to release the electrically conductive fluid from the occluded portion of the anatomical vessel.

2. The method of claim 1, wherein the probe is introduced percutaneously into the anatomical vessel using a guiding member inserted in a central lumen of the probe.

3. The method of claim 1, wherein the occlusive body is expanded by delivering the electrically conductive fluid through a perfusion port in fluid communication with an interior region of the occlusive body.

4. The method of claim 1, wherein the anatomical vessel is a blood vessel.

5. A method for treating tissue, comprising:
   introducing a tissue treatment probe into an anatomical vessel, the tissue treatment probe comprising:
   a probe shaft having a distal end;
   at least one therapeutic electrode carried on the distal end of the probe shaft;
   a first fluid delivery lumen;
   at least one perfusion port on the distal end of the probe shaft in fluid communication with the first fluid delivery lumen; and
   two expandable occlusive bodies carried on the distal end of the probe shaft that are radially expandable from the probe shaft, wherein the at least one perfusion port and the at least one therapeutic electrode are both axially located between the occlusive bodies;
   radially expanding the two occlusive bodies to fully occlude a portion of the anatomical vessel;
   delivering an electrically conductive fluid through the at least one perfusion port into the portion of the anatomical vessel occluded by the radially expanded occlusive bodies;
   therapeutically conveying electrical energy to or from the at least one electrode via the delivered electrically conductive fluid to treat the tissue, wherein the tissue comprises tumorous tissue external to the anatomical vessel; and
   deflating at least one of the two radially expanded occlusive bodies, after the tissue has been treated, to release the electrically conductive fluid from the occluded portion of the anatomical vessel.

6. The method of claim 5, wherein the two occlusive bodies are expanded by delivering the electrically conductive fluid through inflation ports in fluid communication with interior regions of the two occlusive bodies.

7. The method of claim 5, wherein the anatomical vessel is a blood vessel.

8. The method of claim 1, wherein RF energy is conveyed to the plurality of electrodes and wherein the tissue is ablated.

9. The method of claim 5, wherein RF energy is conveyed to the at least one electrode and wherein the tissue is ablated.

* * * * *